United States Patent [19]
Liu

[11] Patent Number: 5,149,617
[45] Date of Patent: Sep. 22, 1992

[54] IMAGEABLE DIACETYLENE ETHERS

[75] Inventor: Kou-Chang Liu, Wayne, N.J.

[73] Assignee: ISP Investments Inc., Wilmington, Del.

[21] Appl. No.: 783,019

[22] Filed: Oct. 25, 1991

Related U.S. Application Data

[62] Division of Ser. No. 601,499, Oct. 23, 1990, Pat. No. 5,094,134.

[51] Int. Cl.$^5$ .................. G03C 1/00; G03C 1/72
[52] U.S. Cl. .................. 430/346; 430/270; 430/281; 430/495
[58] Field of Search .................. 346/762, 135.1; 430/286, 495, 270, 346, 281

[56] References Cited

U.S. PATENT DOCUMENTS

| | | | |
|---|---|---|---|
| 3,723,121 | 3/1973 | Hauser | 430/20 |
| 3,772,028 | 11/1973 | Fico et al. | 430/495 |
| 4,215,208 | 7/1980 | Yee et al. | 526/285 |
| 4,297,470 | 10/1981 | Osada et al. | 526/304 |
| 4,474,807 | 10/1984 | Gerhardt et al. | 514/478 |
| 4,536,473 | 8/1985 | Mihara | 430/575 |
| 4,678,736 | 7/1987 | Hanamura | 430/270 |
| 4,684,688 | 8/1987 | Moskowitz | 524/336 |
| 4,705,742 | 11/1987 | Lewis | 430/333 |
| 4,753,861 | 6/1988 | Tsou et al. | 430/19 |
| 4,863,832 | 9/1989 | Saitoh et al. | 430/281 |
| 4,889,793 | 12/1989 | Taniguchi | 430/284 |
| 5,004,671 | 4/1991 | Nishimura et al. | 430/286 |
| 5,049,428 | 9/1991 | Kanno et al. | 428/64 |

Primary Examiner—Charles L. Bowers, Jr.
Assistant Examiner—John A. McPherson
Attorney, Agent, or Firm—Marilyn J. Maue; Joshua J. Ward

[57] ABSTRACT

This application relates to monomers and homopolymers of diacetylenic ethers having the formula

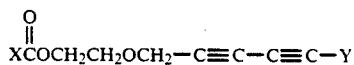

wherein X is alkyl, alkenyl, aryl, alkaryl, aralkyl, aralkenyl, monoalkylamino or dialkylamino and Y is alkyl, alkenyl or

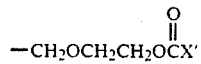

where X' is independently selected from the group of X. The invention also relates to the method of preparing and using said alkoxy diacetylenes.

9 Claims, No Drawings

IMAGEABLE DIACETYLENE ETHERS

This is a division of application Ser. No. 601,499, filed Oct. 23, 1990, now U.S. Pat. No. 5,094,134.

In one aspect this invention relates to novel diacetylene ethers and homopolymers thereof. In another aspect the invention relates to visually imageable monomers and homopolymers which have significantly improved sensitivity to energy transmitted at a short wavelength of 200-350 nm as characterized by photon and particulate radiation and at a wavelength within the 400-1,500 nm range as characterized by lasers, arc lamps, etc. Another aspect relates to high speed data recording by exposure to radiation. Still another aspect of the invention relates to the preparation of the present diacetylenic ethers.

BACKGROUND OF THE INVENTION

Diacetylenic and other polyacetylenic compounds have been used as recording layers for optical discs and similar information storage devices. However, there is a lack of commercially available economical chemicals needed for their preparations. Propargyl alcohol is the only available industrial chemical with a terminal acetylenic functionality. However, diacetylenic chemicals prepared from propargyl alcohol are so inactive that they are impractical for commercial use in recording media. Accordingly, it is an aim of research to discover chemical processes which can be efficiently and economically effected to provide imageable polyacetylenes and their homopolymers.

The development of a visual image which requires exposure at short wavelengths, excludes the economical and efficient laser imaging, since prior polyacetylene compounds are generally incapable of absorbing energy and undergoing polymerization when exposed to light in wavelengths above about 400 nm. Visual images are those images which are clearly recognizable by the human eye and are characterized by high optical contrast in one or more of the red, green and blue portions of the spectrum. By high optical contrast is meant an optical density difference of at least 1.0 between the maximum density and minimum density portions of the image, where optical density is defined as $\log_{10}(1/\text{trans-mittance})$ for transmitted light and $\log_{10}(1/\text{reflectance})$ for reflected light. Such visual imaging is significantly distinguished from prior data recording where image contrast is relatively low and not easily discernable by the human eye or without high magnification. In several cases laser imaging at wavelengths above 400 nm, based on the thermal color change of the polyacetylenic compound to develop a useful visual image, has been attempted, but it has been found that cumbersome high-output equipment, e.g. argon, metal-vapor or gas lasers and the like are required. Relatively low-output lasers, in the 650-1,500 nm wavelength range, fail to imprint on either known polyacetylenes or their polymers, particularly in relatively thick layers required to produce useful visual images as opposed to the relatively thin layers needed for digital data recording.

Short wavelength imaging of prior polyacetylenic compounds is also accompanied with several drawbacks and disadvantages, among which is a lack of color stability at the lower color transition temperatures of the thermochromic compound Also, compounds of significantly greater sensitivity are needed for high definition and contrast in recording data and for production of sharp reproducible images Accordingly, it is the aim of research, with consideration to cost performance and production efficiency, to provide an organic system most suitable for visual imaging and optical data recording, which is imageable at an output energy in the 650-1,500 nm wavelength range characteristic of compact semi-conductor diode lasers or in the short wavelength range characteristic of radiation by UV light, electron beam, α-particles, X-rays, γ-rays, neutrons, etc.

It is an object of this invention to provide a thermochromic or photochromic compound which answers the above needs and which has increased sensitivity to imaging with a compact semi-conductor laser in a wavelength of at least 400 nm or with short wavelength radiation in the 200 to 350 nm range, by a process which has low cost, high performance and high production efficiency.

Another object of this invention is to provide an economical process capable of producing imageable diacetylenic ethers.

Another object of the invention is to provide a transmitted image by a low cost high efficiency process.

Still another object of the invention is to provide an imageable thermosensitive polyacetylene which is receptive to wavelengths up to about 1,500 nm and to a recording film utilizing said polyacetylene.

These and other objects of the invention will become apparent from the following description and disclosure.

THE INVENTION

In accordance with this invention there is provided an imageable thermochromic diacetylene ether having significantly improved sensitivity which is defined by the formula

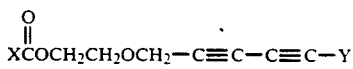

wherein X is a radical having from 1 to 22 carbon atoms and is selected from the group of alkyl, alkenyl, aryl, alkaryl, aralkyl, aralkenyl, monoalkylamino and dialkylamino and Y is alkyl or alkenyl having from 1 to 22 carbon atoms or —CH$_2$OCH$_2$CH$_2$OOCX′ where X′ is independently selected from the group of X.

Of the above diacetylene ethers, the symmetrical diacetylene ether monomers wherein X is a C$_2$ to C$_{10}$ alkylene, carbamate, phenyl or styryl radical, and the homopolymers derived from said monomers, are preferred.

Specific examples of the present diacetylenes include
3,10-dioxa-5,7-dodecadiyn-1,12-bis(n-butylcarbamate),
1,12-(3,10-dioxa-5,7-dodecadiynediyl)dicinnamate,
3,10-dioxa-5,7-dodecadiyn-1,12-bis(n-propylcarbamate),
3,10-dioxa-5,7-dodecadiyn-1,12-bis(ethylcarbamate),
3,10-dioxa-5,7-dodecadiyn-1,12-bis(phenylcarbamate),
1,12-(3,10-dioxa-5,7-octadiynediyl)dibenzoate,
3,10-dioxa-5,7-dodecadiyn-1,12-bis(n-octyl carbamate),
3,10-dioxa-5,7-dodecadiyn-1,12-bis(n-octadecyl carbamate),
3,10-dioxa-5,7-dodecadiyn-1,12-bis(isopropyl carbamate),
3,10-dioxa-5,7-dodecadiyn-1,12-bis(methyl carbamate),
3,10-dioxa-5,7-dodecadiyn-1,12-bis(cyclohexyl carbamate), 3,10-dioxa-5,7-dodecadiyn-1,12-bis(2-methylcarbamyl phenyl carbamate),
3,10-dioxa-5,7-dodecadiyn-1,12-bis[3-(methylamino) carbamyl phenyl carbamate],
1,12-(3,10-dioxa-5,7-dodecadiyne)diyl-di(m-aminobenzoate) and their corresponding homopolymers.

The present ether compounds possess superior photographic properties as observed in their high sensitivity, rapid color transition and high image acuity. As imaging agents, the above diacetylenic ether monomers can be employed individually or in admixtures and such mixtures can comprise combinations of monomers or mixtures of monomeric and homopolymeric compounds of the same or different species. Also the homopolymers themselves may be employed individually or as intermixtures to provide the superior imaging agents of this invention.

As shown hereinafter, diacetylenes prepared by reactions involving propargyl alcohol do not provide sensitive photochromic products which are useful as recording media. It is now found that ethoxylated propargyl alcohol derivatives can be used to produce diacetylene ethers of unexpectedly high sensitivity to short wavelength radiation, e.g. UV light or electron beam exposure and that the homopolymers of such diacetylene ethers achieve permanent color stability and possess high sensitivity to longer wavelength exposure by laser radiation. The symmetrical diacetylene ethers of this invention are prepared by the reaction of an ethoxylated propargyl alcohol having the formula $HC\equiv CCH_2OC_2H_4OH$ with an organic isocyanate, $RNCO$, an ester $RCOOR'$ or a carbamate $R(R'')NCOOR'$ wherein R' at least one of R and R'' is a radical having from 1 to 20 carbon atoms and is selected from the group of alkyl, alkenyl, aryl, alkaryl, aralkyl and aralkenyl and one of R and R'' can be hydrogen to produce the corresponding monoacetylene. The monoacetylene intermediate is then subjected to oxidative coupling with oxygen in the presence of a catalyst, such as cuprous chloride-tetramethylene ethylene diamine. These reactions are illustrated by the following equations:

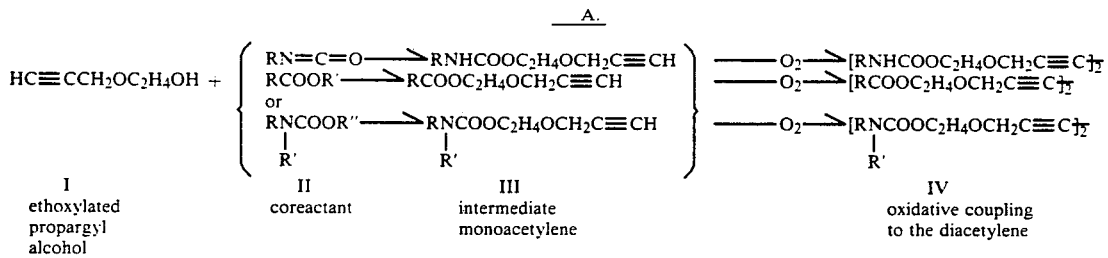

| I | II | III | IV |
|---|---|---|---|
| ethoxylated propargyl alcohol | coreactant | intermediate monoacetylene | oxidative coupling to the diacetylene |

The unsymmetrical diacetylene ethers are prepared by coupling reactions involving the intermediate III above and an acetylenic iodide, exemplified as follows:

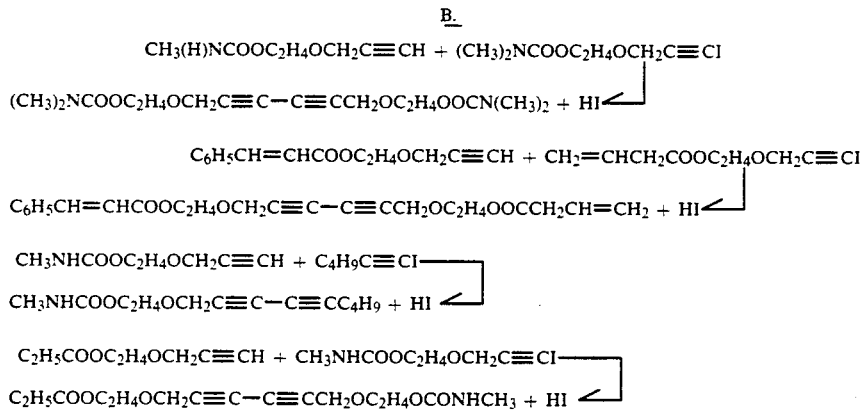

The above reactions are carried out at a temperature of between about 30° and 180° C. under up to about 50 psig for a period of from about 1 to about 40 hours; preferably at a temperature of between about 80° and about 150° C. for a period of from about 2 to about 20 hours. Stoichiometric amounts of reactants I and II or a slight molar excess of coreactant II, e.g. 1:1.2 is employed in the above reaction shown in A.

The homopolymers of the polyacetylene ethers are prepared by subjecting the monomer to radiation in the short wavelength regions of the electromagnetic spectrum.

Where the homopolymer is to be used as a modulating film for imaging master printing plates or printed circuit boards, the homopolymer is subjected to heat, e.g. as generated by radiation emissions at a longer wavelength from a laser or a light source of similar wavelength above 400 nm, such as from a xenon arc lamp, a mercury arc lamp, a tungsten-quartz halogen lamp.

In such applications, e.g. when recording data for transmission to a master printing plate or printed circuit board, it is most desirable to select a diacetylenic ether monomer which undergoes a chromic change which dramatically increases the absorption of blue light (e.g. a chromic change to yellow) since this color change provides the highest contrast for duplication to other photosensitive recording media, particularly those containing photopolymers sensitive to blue and ultraviolet light as are commonly employed in commercial photolithographic printing plates and etch resists used in the preparation of printed circuit boards. The 1,12-(3,10-dioxa-5,7-dodecadiyne)diyl dicinnamate of this invention, having the formula

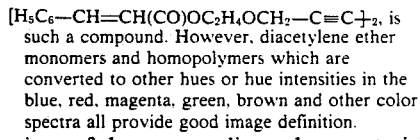

is such a compound. However, diacetylene ether monomers and homopolymers which are converted to other hues or hue intensities in the blue, red, magenta, green, brown and other color spectra all provide good image definition.

Coatings of the present diacetylene materials for application on a substrate are conveniently prepared from aqueous dispersions wherein the diacetylene ether monomers, having an average crystalline diameter of between about 0.02 um and about 5 um, preferably between about 0.1 um and about 1 um, are dispersed in a binder solution, preferably an aqueous binder solution, to provide a dispersion, emulsion or suspension containing from about 1 to about 50 wt. % solids, preferably from about 4 to about 15 wt. % solids. The liquid dispersion of diacetylene ether monomer may then be coated on a substrate and dried. Alternatively, fine homopolymerized particles in a similar dispersion can be coated on the substrate and dried to provide the imageable film of this invention. Other coating alternatives to the dispersion layer coating include the deposition of one or more monomolecular layers of the diacetylene ether monomer and/or homopolymer as is carried out by the Langmuir-Blodgette technique, spin or spray coating methods.

Suitable diacetylene ether substrates include polyethylene terephthalate, nylon, polystyrene, cellulose acetates, cellulose nitrate, cellophane, polyvinyl chloride, polyvinylidene chloride, teflon, polychlorotrifluoroethylene, polyethylene, polypropylene, paper, ceramic, glass, metal, wood and the like.

For the purposes of the present invention, the image receptive layer is usually the surface layer of the imaging film; however, a protective layer can be applied over the diacetylene ether surface layer, e.g. to prevent damage due to abrasion, moisture, etc. Liquid dispersion of normally crystalline diacetylenic ethers may be aged before drying on the substrate according to the process disclosed in U.S. Pat. No. 4,734,355.

Exemplary of binder materials for use in dispersions include natural and synthetic plastics, resins, waxes, colloids, gels and the like including gelatins, desirably photographic-grade gelatin, various polysaccharides including dextran, dextrin, hydrophilic cellulose ethers and esters, acetylated starches, natural and synthetic waxes including paraffin, beeswax, polyvinyl-lactams, polymers of acrylic and methacrylic esters and amides, hydrolyzed interpolymers of vinyl acetate and unsaturated addition polymerizable compounds such as maleic anhydride, acrylic and methylacrylic esters and styrene, vinyl acetate polymers and copolymers and their derivatives including completely and partially hydrolyzed products thereof, polyvinyl acetate, polyvinyl alcohol, polyethylene oxide polymers, polyvinylpyrrolidone, polyvinyl acetals including polyvinyl acetaldehyde acetal, polyvinyl butyraldehyde acetal, polyvinyl sodium-o-sulfobenzaldehyde acetal, polyvinyl formaldehyde acetal, and numerous other known photographic binder materials, or mixtures of binder materials, including a substantial number of aforelisted useful plastic and resinous substrate materials which are capble of being placed in the form of a dope, solution, dispersion, gel, or the like for incorporation therein of the thermosensitive polyacetylenic polymer and capable of processing to a solid form containing dispersed crystals of the thermosensitive crystalline polyacetylenic polymer. As is well known in the art in the preparation of smooth uniform continuous coatings of binder materials, there may be employed therewith small amounts of conventional coating aids as viscosity controlling agents, surface active agents, leveling agents dispersing agents and the like.

The dried imageable, monomeric diacetylene ether film of this invention is subjected to exposure by radiant photon, ionizing or particulate energy transmitted at a wavelength of between about 200 and about 350 nm to effect an immediate color change, or a discernable change in color intensity, by homopolymerization of the monomer. This short wavelength exposure can be effected with UV light, $\alpha$-particles, X-rays, $\gamma$-rays, $\beta$-rays, an electron beam, neutrons, a xenon flash lamp, a mercury arc lamp, a tungsten quartz, halogen lamp, actinic light, a UV laser e.g. an argon ion, a krypton ion or a GaAlP laser, and the like. For example, when using an electron beam, the image receptive layer is subjected to a dosage of between about $10^{-10}$ and about $10^{-1}$ coulomb/cm$^2$ (C/cm$^2$), preferably between about $10^{-8}$ and about $10^{-3}$ C/cm$^2$, or equivalent dosage for other sources of particulate or photon energy radiation, to produce an immediate image of distinguishable color or color intensity. Generally short wavelength energies of between about 10 and about 50 KeV can be employed to image the polyacetylene diethers of this invention.

Specific techniques of short wavelength recording are well known, thus further amplification is not required. However, for illustrative purposes, a conventional electron beam recording operation suitable for the present invention may utilize an electron beam characterized by having a beam diameter of from about 1 to 100 micrometers, an energy of from about 10 to 30 KeV, a current flow of from about $10^{-9}$ to $10^{-5}$ amps and adapted to scan a target area at a rate such that the dwell time is from about $10^{-8}$ to $10^{-3}$ seconds. Vacuum pressures in the film chamber commonly range from about $10^{-3}$ to $10^{-8}$ torr.

When a homopolymer of the diacetylene ether is applied as the imageable layer on a substrate, it is directly imaged in a particular pattern or design, with a laser in the writing mode generating energy at a wavelength of above 400 nm. Lasers such as semi-conductor, solid state, gas, metal-vapor and dye lasers in pulsed or continuous wave can be used, although semi-conductor diode lasers having an output power of from about 1 microwatt to 10 watts are preferred. Specific examples of suitable lasers include GaAlAs, NaYtAl garnet, Ar, He-Ne, He-Cd, GaAs NeYAl garnet, ruby, NaYAg, krypton ion, copper vapor lasers, etc.

Lasers, or other light sources, transmitting energy above 400 up to 1,500 nm or more wavelength provide thermal imaging at high image resolution, which is an important consideration when recording data. Within the wavelength range of 600 to 1,500 nm, high speed can be achieved as well. For example, using a lser beam diameter of 0.5 to 2 um, an exposure time of 180-250 ns/dot and output of 2.5-3.5 mW, an image is encoded on the diacetylene ether homopolymer which has excellent resolution and high color contrast. Generally the speed of recording and density varies directly with the output power of the laser and the thickness of the polymer coating. Accordingly, thin coatings of from about 0.02 to 100 micrometers, preferably from about 0.1 to 5 micrometer are recommended, whereupon the optical density change within the imaged area is from about 1.0 to greater than 5.0 density units and preferably from about 1.5 to about 4.5 density units.

It is to be understood that the polymeric diacetylenic ethers are usually highly colored and strongly absorb radiation across a broad range of the visible spectrum from 400-650 nm. However, it is also to be understood that in cases where a certain homopolymer does not absorb radiation in the wavelength of a given laser emission, a suitable energy absorbing compound is used in conjunction with the homopolymer in the coating to absorb energy from the laser and to generate heat generally in excess of 50° C., preferably in excess of 80° C., for effecting the thermal color change or change in color intensity in the impinged portions of the thermochromic diacetylene ether homopolymer. Such energy absorbing compounds are generally needed to inscribe a homopolymer when the wavelength of the laser radiation is more than about 650 nm or when it is desirable to encode the diacetylene ether monomer at energies in excess of 380 nm wavelength.

Suitable energy absorbing compounds include complex and quaternized dyes such as the polycarbocyanine dyes disclosed in copending U.S. patent application Ser. No. 07/601,537 entitled LASER IMAGEABLE COMPOSITION incorporated herein by reference. Other suitable energy absorbing dyes include metal complexes such as diimine iron complex, dithiol nickel complex, indigo, anthraquinone, azulenium, polycarbocyanine, squarylium, indolizinium, naphthalocyanine, naphthoquinone and its analogs, phthalocyanine, polymethine, pyrylium, thiapyrylium, telluropyrylium, triaryl ammonium, triquinocycloalkane, or the specific dyes disclosed in the Journal of Imaging Science, Volume 32, number 2, March/April 1988, pages 51-56 (ORGANIC ACTIVE LAYER MATERIALS FOR OPTICAL RECORDING by James E. Kuder); Chemistry in Britain, November 1986, pages 997-1000 (MODERN DYE CHEMISTRY by J. Griffiths); Angewandte Chemie, Volume 28, number 6, June 1989, pages 677-828 (SEARCH FOR HIGHLY COLORED ORGANIC COMPOUNDS by Jurgen Fabian et al.); Journal of Imaging Technology, Volume 12, Number 3, June 1986, pages 140-143, (ORGANIC MATERIALS FOR OPTICAL DATA STORAGE MEDIA—AN OVERVIEW by James E. Kuder), and Kirk-Othmer's Encyclopedia of Chemical Technology, Second Edition, Vol. 6, pages 605-609 and 611-624, all incorporated herein by reference.

As a guide for the selection of an energy absorbing compound in a wavelength similar to transmission of a particular imaging device, the following table provides specific examples of wavelength absorbance. However, these dyes are in no way limiting to the scope of energy absorbing compounds useful in this invention.

TABLE

| Dye | Wavelength Absorption |
| --- | --- |
| Aromatic annulenes | 768 nm |
| Al tetraazaporphyrins | 1204 nm |
| Ni dithiolenes | 1298 nm |
| Streptopolymethines | 1500 nm |
| Silenoxanthenylium | 802 nm |
| Azo | 778 nm |
| Indophenols and Analogues | 761 nm |
| Thermochromic dianthrone | 675 nm |
| Betaines | 934 nm |
| Divinyl benzothiazole | 640 nm |
| Trivinyl benzothiazole | 750 nm |

TABLE-continued

| Dye | Wavelength Absorption |
| --- | --- |
| Diethyl carbocyanine iodide | 700 nm |

Preferred of the above compounds are the water soluble dyes, most preferably the water soluble polycarbocyanine dyes. It is also to be understood that mixtures of these dyes can be employed. For example, 1:20 to 20:1 mixtures of polycarbocyanine and squarylium dye mixtures are useful and can provide the energy absorption and heat needed to thermally activate the thermosensitive dialkoxy polyacetylene homopolymer at these higher wavelength transmissions. When needed, the energy absorbing adjuvant is added and intimately mixed in the dispersion prior to coating and drying on the substrate. The amount of dye employed is sufficient to provide a peak optical density of between about 0.1 and about 3, preferably between about 0.2 and about 2, in the dried coating. In cases where the dye is not water soluble it can be dissolved in a suitable inert solvent such as a ketone, alcohol, ester, hydrocarbon etc. and the like for addition to the dispersion. The most preferable solvents are those which are water miscible.

In such cases where an energy absorbing dye is employed, the weight ratio of homopolymer to dye can vary between about 1000:1 and about 1:10, depending upon the amount of homopolymer present and the amount of radiation energy needed to be converted to heat energy. Most often the dye comprises between about 0.005 and about 1 wt. % of the imaging compound.

With regard to imaging techniques, the short wavelength exposure from about 200 to about 350 nm, can be employed to homopolymerize all or a portion of the colorless diacetylene ether monomer, i.e. a short wavelength transmitting device can be used to homopolymerize the entire colorless monomer (case a) or the monomer can be scribed, in one or several steps, to define a predetermined pattern or image with a short wavelength transmitting device, operated in the writing mode, (case b). In case (a), the entire film acquires chromic change associated with the particular homopolymer; whereas in case (b) a homopolymerized chromic image is inscribed on the colorless background of the unexposed monomer. In case (a) the laser generating energy in a wavelength above 400 nm is employed in the writing mode to inscribe a predetermined permanent image of a distinguishable color on the contrasting colored homopolymer layer. In case (b), the laser generating at the longer wavelength can be synchronized with the scribing device operating at the short wavelength and used in the writing mode to retrace the previously inscribed image or it can be used to expose the entire polymerized and non-polymerized portions of the diacetylene ether layer so as to induce a permanent chromic change to the preinscribed image on a colorless background.

Having thus generally described the invention, reference is now had to the following examples which illustrate preferred embodiments but which are not to be construed as limiting to the scope of the invention which is more broadly defined above and in the appended claims.

EXAMPLE 1

3,10-dioxa-5,7-dodecadiyn-1,12-bis(n-propyl carbamate)

2-(Propargyl) ethanol (100 g, 1 mole), tetramethylethylenediamine (30 g) and tetrahydrofuran (THF) (400 ml) were charged into a 1-liter flask which was equipped with a mechanical stirrer, thermometer, gas inlet, and a dry ice condenser. The solution was brought to 50° C. under a blanket of nitrogen. A solution of n-propyl isocyanate (112 g, 1.2 moles) and THF (50 ml) was added through a dropping funnel to the above solution which was vigorously stirred over a period of one hour at 50° to 55° C. The resulting solution was held for 23 hours at this temperature and then cooled to 40° C. Cuperous chloride (3 g) was then added and oxygen was bubbled through the solution at 40–45° C. for 23 hours after which the solvent was stripped off under vacuum and the remaining solid material was washed twice with 300 ml of 10% HCl, twice with 300 ml of distilled water and air dried to give 165.4 g of 3,10-dioxa-5,7-dodecadiyn-1,12-bis(n-propyl carbamate); m.p. 93–94° C. A one gram sample of the colorless crystalline product was spread on a filter paper and subjected to a UV irradiation at 254 nm. In less than 1 second the colorless, crystalline product homopolymerized to a dark purple. Upon heating on a hot plate, the purple polydiacetylene underwent a thermochromic change to a permanent red color.

EXAMPLE 2

3,10-dioxa-5,7-dodecadiyn-1,12-bis(ethyl carbamate)

3,10-dioxa-5,7-dodecadiyn-1,12-bis(ethyl carbamate) was prepared following the same procedure as for the preparation of 3,10-dioxa-5,7-dodecadiyn-1,12-bis(n-propyl carbamate) in Example 1 except that ethyl isocyanate was substituted for n-propyl isocayanate. The 3,10-dioxa-5,7-dodecadiyn-1,12-bis(ethyl carbamate) product recovered has a melting point of 105–107° C.

A one gram sample of the crystalline product was spread on a filter paper and subjected to a UV irradiation at 254 nm. Within less than one second, the colorless crystalline solid product homopolymerized to a blue color which, upon heating on a hot plate, underwent a thermochromic change to a permanent red color.

EXAMPLE 3

3,10-dioxa-5,7-dodecadiyn-1,12-bis(isopropyl carbamate)

A 180 g sample of 3,10-dioxa-5,7-dodecadiyn-1,12-bis(isopropyl carbamate) was prepared following the same procedure as for the preparation of 3,10-dioxa-5,7-dodecadiyn-1,12-bis(n-propyl carbamate) in Example 1 except that isopropyl isocyanate was substituted for n-propyl isocayanate. The 3,10-dioxa-5,7-dodecadiyn-1,12-bis(isopropyl carbamate) product recovered has a melting point of 82–85° C.

A one gram sample of the crystalline product was spread on a filter paper and subjected to a UV irradiation at 254 nm. Within less than one second, the colorless crystalline solid product homopolymerized to a pink color which, upon heating on a hot plate, underwent a thermochromic change to a permanent golden yellow color.

EXAMPLE 4

3,10-dioxa-5,7-dodecadiyn-1,12-bis(n-butyl carbamate)

2-(Propargyl) ethanol (1.5 mole), tetramethylethylenediamine (30 g) and (THF) (500 ml) were charged into a 2-liter flask which was equipped with a mechanical stirrer, thermometer, gas inlet, and a dry ice condenser. The solution was brought to 60° C. under a blanket of nitrogen. A solution of n-butyl isocyanate (1.65 moles) and THF (200 ml) was added through a dropping funnel to the above solution which was vigorously stirred over a period of one hour at 60° to 68° C. The resulting solution was held for 3 hours at this temperature and then cooled to 40° C. Cuperous chloride (10 g) was then added and oxygen was bubbled through the solution at 40–45° C. for 20 hours after which the solvent was stripped off under vacuum and the remaining solid material was washed twice with 300 ml of 10% HCl, twice with 300 ml of distilled water and air dried to give 389.6 g of 3,10-dioxa-5,7-dodecadiyn-1,12-bis(n-butyl carbamate); m.p. 80–82° C. A one gram sample of the colorless crystalline product was spread on a filter paper and subjected to a UV irradiation at 254 nm. In less than 1 second the colorless, crystalline product homopolymerized to a dark purple. Upon heating on a hot plate, the purple polydiacetylene underwent a thermochromic change to a permanent red color.

EXAMPLE 5

A. Preparation of [C<sub>6</sub>H<sub>5</sub>CH=CH—COOC<sub>2</sub>H<sub>4</sub>OCH<sub>2</sub>—C≡C—]<sub>2</sub>-

Trans methyl cinnamate (324.4 g, 2 moles), 2-(propargyloxy) ethanol (200.1 g) and concentrated sulfuric acid (1 ml) were charged into a one-liter flask equipped with a mechanical stirrer, a thermometer, a nitrogen inlet and an adapter connected to a condenser. The solution was held at 110° C. over night under a flowing stream of nitrogen to remove methanol by-product. The remaining liquid was then vacuum distilled and a center cut of 280.7 g was collected at 147° C. and 0.01 mm Hg. The 2-(propargyloxy) ethanol product in 98% purity was recovered and identified by IR and nmr analysis.

2-(Propargyloxy) ethanol (78.1 g), tetrahydrofuran (340 ml), tetramethyl ethylene diamine (20 g) and cuperous chloride (3 g) were charged into a one-liter flask. A stream of oxygen was bubbling through the solution with vigorous stirring for 11 hours at 40–45° C. The tetrahydrofuran solvent was then stripped off. The crude product was washed two times with 300 ml of 10% HCl solution and two times with water. After being dried in air, 72.5 g of 2-(propargyloxy) ethyl cinnamate, m.p. 62–65° C. was obtained. The structure of the chemical was identified by nmr and IR analyses.

B. Preparation of Coating Dispersion

In a glass container, 1.2 g. of the above product were dissolved at about 50° C. in 3.6 g. of ethyl acetate and the resulting solution was filtered and designated Solution A. A second solution, designated Solution B, was prepared by dissolving 1.2 g. of photographic gelatin and 0.05 g. of ALKANOL XC (an alcohol-containing wetting agent, supplied by E. I. duPont) in 30 g. of water. Solution B was heated to 60° C. and introduced into a 250 ml Waring Blender. While blending at high speed, Solution A was added to Solution B after which the blending was continued for 2 minutes. The resulting mixture was then poured into a crystallizing dish to chill set at about 12° C. The resulting gelled dispersion was then cut into approximately 1 cm cubes and allowed to warm in an air stream at approximately 32° C. to remove ethyl acetate by evaporation. After the ethyl acetate had been removed the gelled dispersion was reconstituted by melting at 40° C. and adding sufficient water to replace the weight loss that occurred during drying.

C. Coating a Film Base with Dispersion

The reconstituted dispersion was coated at about 8 micrometers thickness on a poly(ethylene terephthalate) film base which had been overcoated with a 1 micrometer thick layer of an adhesion promoting material composed of about 50 wt. % gelatin and 50 wt. % of a latex polymer. The coated film was then allowed to dry in air at ambient temperature.

D. Imaging the Film

A 4×4 inch sample of the above film was placed in a holding device over which is mounted a low pressure mercury arc lamp having a 100 watt output and emitting UV radiation at a maximum wavelength of about 253.7 nm. The colorless film is exposed for 0.1 second to emissions from the lamp so as to absorb energy and polymerize colorless $[C_6H_5-CH=CHCOOC_2H_4OCH_2C\equiv C]_2$ to a rich magenta homopolymer.

The resulting homopolymer is then scribed with a copper vapor laser having an output of 3 watts which transmits energy at about 560 nm wavelength and impinges discrete areas of the surface of the film defined by a series of diamond shaped figures and lines. The energy generated by this transmission is absorbed by the homopolymer and heats the exposed areas of the film to a temperature of about 65° C. in a fraction of a second whereby an image of said diamond shaped figures and lines is transmitted in high acuity in a permanent bright yellow color on the magenta background which is not exposed to the laser emissions.

E. Use of the Yellow Imaged Film as a Modulating Film

The above sample is employed as a modualting film in the following test. A blue light source, i.e. a high pressure mercury arc lamp operating at an output power of 1 kilowatt and transmitting energy in a wavelength of 350-450 nm is focused to scan the entire area of the film sample which is positioned about 3.6 feet from the light outlet. Contiguous with the surface of the film and on the surface directly opposite the surface being radiated, is positioned the imageable surface layer, i.e. 4-diazodiphenylamine/formaldehyde condensate, supported on cellulose triacetate sheet of the photoresist master printing plate.

The blue light from the lamp is absorbed in the imaged areas of the film sample and is transmitted from the non-imaged areas, in an exact negative imaged pattern to the imageable surface layer of the photoresist where it attacks the polymer condensate and renders the decomposed areas insoluble in water.

EXAMPLE 6

2,4-hexadiyn-1,6-bis(n-butyl carbamate)

Propargyl alcohol (104.9 g, 1.9 moles), tetramethylethylenediamine (28.1 g) and (THF) (365.5 ml) were charged into a 1-liter flask which was equipped with a mechanical stirrer, thermometer, gas inlet, and a dry ice condenser. The solution was brought to 40° C. under a blanket of nitrogen. A solution of n-butyl isocyanate (222.7 g, 2.3 moles) and THF (93 ml) was added through a dropping funnel to the above solution which was vigorously stirred over a period of one hour at 40° to 45° C. The resulting solution was held for 18 hours at this temperature. Cuperous chloride (8 g) was then added and oxygen was bubbled through the solution at 40-45° C. for 28 hours after which the solvent was stripped off and the remaining solid material was washed twice with 300 ml of 10% HCl, twice with 300 ml of distilled water and air dried to give 280.5 g of 2,4-hexadiyn-1,6-bis(n-butyl carbamate). The colorless, crystalline product has a m.p. of 55-60° C. A one gram sample of the colorless crystalline product was spread on a filter paper and subjected to a UV irradiation at 254 nm. After 2 seconds only a slight color change could be detected indicating that this product would be unsuitable for photoimaging.

EXAMPLE 7

2,4-hexadiyn-1,6-bis(ethyl carbamate)

A 176 g. sample of 2,4-hexadiyn-1,6-bis(ethyl carbamate) was prepared following the same procedure as for the preparation of 2,4-hexadiyn-1,6-bis(n-butyl carbamate) in Example 6 except that ethyl isocyanate was substituted for n-propyl isocayanate. The 2,4-hexadiyn-1,6-bis(ethyl carbamate) colorless crystalline product recovered has a melting point of 93-94° C.

A one gram sample of the product was spread on a filter paper and subjected to a UV irradiation at 254 nm. After 5 seconds, the colorless crystalline product homopolymerized to a magenta color. Upon heating the homopolymer on a hot plate the product gradually darkened. Because of the slow reactivity to the homopolymer and the lack of a sharp thermochromic change, this product is unsuitable for photoimaging.

EXAMPLE 8

2,4-hexadiyn-1,6-bis(n-propyl carbamate)

A 281 g sample of 2,4-hexadiyn-1,6-bis(n-propyl carbamate) was prepared following the same procedure as for the preparation of 2,4-hexadiyn-1,6-bis(n-butyl carbamate) in Example 6 except that n-propyl isocyanate was substituted for n-butyl isocayanate. The 2,4-hexadiyn-1,6-bis(n-propyl carbamate) colorless, crystalline product recovered has a melting point of 115-117° C.

A one gram sample of the product was spread on a filter paper and subjected to a UV irradiation at 254 nm. After 30 seconds, no color change was observed, accordingly this product is unsuitable for photoimaging.

EXAMPLE 9

2,4-hexadiyn-1,6-bis(isopropyl carbamate)

A 28 g sample of 2,4-hexadiyn-1,6-bis(isopropyl carbamate) was prepared following the same procedure as for the preparation of 2,4-hexadiyn-1,6-bis(n-butyl carbamate) in Example 6 except that isopropyl isocyanate was substituted for n-butyl isocayanate. The 2,4-hexadiyn-1,6-bis-(isopropyl carbamate) colorless, crystalline product recovered has a melting point of 138-140° C.

A one gram sample of the product was spread on a 5 inch filter paper and subjected to a UV irradiation at 254 nm. After 30 seconds no color change was observed, indicating that this product is unsuitable for photoimaging.

EXAMPLE 10

2,4-hexadiyn-1,6-diyl dicinnamate 2,4-Hexadiyn-1,6-diol (66.1 g, 0.6 mole), triethylamine (70 g) and (THF) (400 ml) were charged into a 1-liter flask which was equipped with a mechanical stirrer, thermometer, gas inlet, and a dry ice condenser. The solution was brought to 50° C. under a blanket of nitrogen. A solution of cinnamoyl chloride (110 g, 0.6 moles) and THF (200 ml) was added through a dropping funnel to the above solution which was vigorously stirred over a period of one hour at 45°. The resulting solution was held for 5 hours at this temperature and then heated to 55° C. and held at this temperature for an additional 20 hours to complete the reaction, after which the THF was stripped off and the remaining solid was redissolved in 500 ml of toluene. The toluene solution was washed three times with water, dried over magnesium sulfate and filtered After the toluene was removed from the filtrate, 134 g. of the colorless, crystalline 2,4-hexadiyn-1,6-diyl dicinnamate product having a m.p. of 102-104° was identified by NMR and IR analyses. One gram of the dicinnamate was spread on a filter paper and subjected to UV irradiation at 254 nm. After 30 seconds, no color change was observed; indicating that this product is unsuitable for photoimaging.

EXAMPLE 11

Example 5 is repeated except that in Part B, 0.1 wt. % of IR-125 dye (a polycarbocyanine dye supplied by Eastman Kodak) is added to solution B and a GaAlAs semiconductor diode laser with a wavelength of about 830 nm is substituted for the copper vapor laser in Part D. The image produced is one of high resolution defined in a bright yellow color on a magenta colored background.

EXAMPLE 12

Example 5 is repeated except that in part D, an electron beam writing device is used in place of the high pressure mercury arc lamp. The electron beam is used to instantly homopolymerize diacetylene and to write an image consisting of a series of lines by homopolymerizing the diacetylene cinnamate monomer in the corresponding discrete areas of exposure. The image is instantly visible as magenta lines on a colorless non-exposed monomer background. After about 1 hour, in the same manner, dots between the magenta lines are inscribed on the film with the electron beam scriber to provide a magenta image of lines and dots on the unexposed colorless background Also in Part D, a broad exposure of the entire film is made with the copper vapor laser instead of impinging discrete areas. Within a fraction of a second the well defined image of the magenta lines and dots is transformed to a permanent bright yellow image.

TABLE I

| | Comparison of Diacetylene Diether Products | |
|---|---|---|
| Example | UV Exposure* Sensitivity/Color | heat Permanent Color |
| 1 | high/purple | red |
| 2 | high/blue | red |
| 3 | high/pink | intense golden yellow |
| 4 | high/purple | red |
| 5 | high/magenta | intense golden yellow |
| 6 | low/pale yellow | — |
| 7 | low/magenta | — |
| 8 | inactive** | |
| 9 | inactive** | — |
| 10 | inactive** | — |

*a mercury lamp, Mineralight ®, Model USV-54 operating at about 254 nm wavelength
**no observable color after 30 seconds It is to be understood that many modifications and substitutions can be made in the above examples without departing from the scope of this invention. For example, any of the other monomers or homopolymers of diacetylene ethers described herein can be substituted in any one of the corresponding examples to prepare films which upon imaging, provide a desired pattern or data recording in high acuity and sharp contrast. Further, any of the other radiation devices which transmit energy in a short wavelength of 200-350 nm and/or any of the lasers which transmit energy in the longer wavelength above 350 nm can be substituted in any of the corresponding examples in accordance with the teachings of this invention. Also any of the energy absorbing heat transmitting dyes including other polycarbocyamine dyes, squarilium or pyrilium dyes and dye complexes or mixtures mentioned or described in copending U.S. patent application Ser. No. 07/601,532, filed concurrently herewith, and in U.S. Pat. No. 4,513,071, which absorb energy in a wavelength similar to that of the energy generated from the laser, can be substituted in the appropriate examples or examples indicated by the above substitutions. Additionally, any of the other photoresist coatings for an image receiving device can be made without departing from the scope of this invention.

What is claimed is:

1. An imageable film comprising a substrate on which is supported an imageable layer of the diacetylene ether having the formula

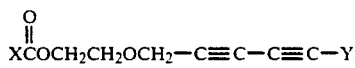

wherein X is a radical having from 1 to 22 carbon atoms and is selected from the group of alkyl, carbamate, alkenyl, aryl, phenylamino, alkaryl, aralkyl, aralkenyl, monoalkylamino and dialkylamino and Y is alkyl or alkenyl having from 1 to 22 carbon atoms or —CH$_2$OCH$_2$CH$_2$OOCX' where X' is independently selected from the group of X.

2. The film of claim 1 in which X of said diacetylene ether is alkyl, carbamate, phenyl or styryl and Y is —CH$_2$OCH$_2$CH$_2$OOCX'.

3. The film of claim 1 in which said diacetylene ether has the symmetrical structure

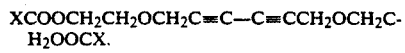

4. The film of claim 1 in which said diacetylene ether is a mixture of said diacetylene ether compounds.

5. The film of claim 1 in which said diacetylene ether has the formula

6. The film of claim 1 in which said diacetylene ether has the formula $[(CH_3)_2CHNHCOOC_2H_4OCH_2C{\equiv}C\!\!-\!]_2$.

7. The film of claim 1 in which said diacetylene ether has the formula $[CH_3NHCOOC_2H_4OCH_2C{\equiv}C\!\!-\!]_2$.

8. The film of claim 1 in which said diacetylene ether has the formula $[C_6H_5{-}NHCOOC_2H_4OCH_2C{\equiv}C\!\!-\!]_2$.

9. The film of claim 1 in which said diacetylene ether has the formula $[C_6H_5{-}COOC_2H_4OCH_2C{\equiv}C\!\!-\!]_2$.

* * * * *